(12) United States Patent  
Simms, Jr.

(10) Patent No.: US 7,353,063 B2  
(45) Date of Patent: Apr. 1, 2008

(54) GENERATING AND COMMUNICATING WEB CONTENT FROM WITHIN AN IMPLANTABLE MEDICAL DEVICE

(75) Inventor: Howard D. Simms, Jr., Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 453 days.

(21) Appl. No.: 11/020,937

(22) Filed: Dec. 22, 2004

(65) Prior Publication Data

US 2006/0136014 A1   Jun. 22, 2006

(51) Int. Cl.
*A61N 1/08* (2006.01)

(52) U.S. Cl. .............. 607/32; 607/30; 607/60
(58) Field of Classification Search ........... 607/60, 607/32; 600/300; 128/899
See application file for complete search history.

(56) References Cited

U.S. PATENT DOCUMENTS 6,101,407 A * 8/2000 Groezinger ............. 600/407
6,250,309 B1   6/2001 Krichen et al. ............. 128/899
6,473,638 B2  10/2002 Ferek-Petric ............... 600/523
6,612,984 B1 * 9/2003 Kerr, II ..................... 600/300
6,644,322 B2 * 11/2003 Webb ......................... 128/899
6,934,698 B2 * 8/2005 Judd et al. ..................... 707/1

* cited by examiner

*Primary Examiner*—Carl Layno
*Assistant Examiner*—Natasha Patel
(74) *Attorney, Agent, or Firm*—Schwegman, Lundberg, & Woessner, P.A.

(57) ABSTRACT

Methods, systems, and computer program products for generating and communicating web content from within an implantable medical device are provided. A method includes collecting data from a memory and/or subsystem of an implantable medical device. Upon collecting the data, the data is converted into web content having a web readable format that is readily consumable for display via a web interface thereby providing a web server from within the implantable medical device. The structure of an output file may be populated with the data converted into the web content. The method may further include transmitting the output file from the implantable medical device to a computing apparatus.

34 Claims, 7 Drawing Sheets

GENERATING AND COMMUNICATING WEB CONTENT FROM WITHIN AN IMPLANTABLE MEDICAL DEVICE

FIELD OF INVENTION

The present invention relates generally to medical devices and appliances for interfacing with medical devices. More particularly, the present invention is directed to generating and communicating web content from within implanted medical devices.

BACKGROUND OF THE INVENTION

Medical devices, including pulse generators such as pacemakers and implantable cardiac defibrillators, are frequently involved in activities that call for the sharing of pertinent information regarding the medical device and/or the patient utilizing the medical device. In order to support implanted medical devices in previous systems, special purpose data interpretation software running on an external programmer or a central server needs to be replicated and/or extended to account for implanted medical device data formats. The central server also manages large volumes of patient data from around the world. The data interpretation software is used for translating information received from the medical device into a human-readable format before making the information available to users.

Further, external programmer application software and server-based implanted medical device data interpretation software must contain logic to process data from multiple medical device models within a family. For example, not all features are available in all models, thus, the external software must account for this variety of features in rendering data for display to a physician. Therefore, both the need for the device specific data interpretation software and the need to account for a variety of features available between models significantly increase the size, burden, and cost of the applications executing on the central server and/or external programmer.

Still further, because the recorded medical device data has a tendency to be in a proprietary format, the integration of the data with the clinical practice of outside entities, such as hospitals and clinics, is difficult due to issues of incompatibility with proprietary data formats.

Additionally, legacy systems require data to be collected by a programmer or medical instrument before it can be translated and readably presented to a user. Some legacy systems require a network to be present in order to display data using a web interface.

It is with respect to these and other considerations that the present invention has been made.

SUMMARY OF THE INVENTION

In accordance with the present invention, the above and other problems are solved by embodiments of the present invention. Embodiments of the present invention are directed to methods, systems, and computer program products for generating and communicating web content from within a medical device. The present invention provides an internet-ready data exchange mechanism that is integrated into an implanted medical device. The data exchange mechanism facilitates distribution of information to pervasive computing apparatuses, such as computing devices and/or computing systems that can retrieve data directly from the implanted medical device. The present invention addresses problems such as, but not limited to, those mentioned above by generating and communicating ready-to-use web pages as an output. For example, the ready-to-use web pages may be based on Standard Generalized Markup Language (SGML), a system for organizing and tagging elements of a document. SGML includes derivatives such as HTML, or extensible markup language (XML) with an extensible style language (XSL) file or style sheet that can be used to generate hypertext markup language (HTML) output. Thus, the present invention eliminates the need for external software to contain the logic for translating and presenting the data to a user.

One embodiment of the present invention is a method for generating and communicating web content from within an implantable medical device. The method involves collecting data from a memory and/or subsystem of the implantable medical device. The data is then converted into web content having a web readable format that is readily consumable for display via a web interface. A structure of an output file is populated with the data converted into the web content thereby providing a web server from within the implantable medical device.

Another embodiment of the present invention is a computer program product including a computer usable medium having control logic stored therein for causing a pulse generator to generate and communicate web content. The control logic includes computer readable program code for causing the pulse generator to collect data from a memory of the pulse generator, convert the data into web content having a web readable format that is readily consumable for display via a web interface, and populate a structure of an output file with the data converted into the web content. The computer program product may further include computer program code for causing the pulse generator to transmit the output file to a computing device wherein the output file is stored in the memory of the pulse generator.

Still another embodiment of the present invention is a system for generating and communicating web content from within an implantable medical device. The system includes the implantable medical device operative to collect data from at least one subsystem of the medical device. The implantable medical device is further operative to convert the data into web content having a web readable format that is readily consumable for display via a web interface and populate a structure of an output file with the data converted into the web content. The system may further include a computing device where the implantable medical device is further operative to transmit the output file to the computing device.

These and various other features as well as advantages, which characterize the present invention, will be apparent from a reading of the following detailed description and a review of the associated drawings.

DETAILED DESCRIPTION

As described briefly above, embodiments of the present invention provide methods, computer program products, and systems for generating and communicating web content from within implantable medical devices. Generating and communicating web content from within an implantable medical device eliminates the need for software external to the medical device to contain logic for translating and presenting data generated at the medical device in a human-readable format. Further, embodiments the present invention remove the need for external software to account for a variety of features that differ between medical device models. Still further, embodiments of the present invention allow for distribution of the web content generated to other medical information systems for patient monitoring and clinical management. In the following detailed description, references are made to accompanying drawings that form a part hereof, and in which are shown by way of illustration specific embodiments or examples. These embodiments may be combined, other embodiments may be utilized, and structural changes may be made without departing from the spirit and scope of the present invention. The following detailed description is, therefore, not to be taken in a limiting sense, and the scope of the present invention is defined by the appended claims and their equivalents.

Referring now to the drawings, in which like numerals represent like elements through the several figures, aspects of the present invention and the exemplary operating environment will be described. FIGS. 1-7 and the following discussion are intended to provide a brief, general description of a suitable computing environment in which the embodiments of the invention may be implemented. While the invention will be described in the general context of program modules that execute to generate and communicate web content from within medical devices, those skilled in the art will recognize that the invention may also be implemented in combination with other program modules.

Generally, program modules include routines, programs, components, data structures, and other types of structures that perform particular tasks or implement particular abstract data types. Moreover, those skilled in the art will appreciate that the invention may be practiced with other computer system configurations, including hand-held devices, multi-processor systems, microprocessor-based or programmable consumer electronics, minicomputers, mainframe computers, and the like. The invention may also be practiced in distributed computing environments where tasks are performed by remote processing devices that are linked through a communications network. In a distributed computing environment, program modules may be located in both local and remote memory storage devices.

The present embodiments of the invention will be described in applications involving implantable medical devices including, but not limited to, implantable cardiac rhythm management systems such as pacemakers, defibrillators, and biventricular or other multi-site coordination devices. However it is understood that the present methods, systems, and computer program products may be employed in un-implanted devices, including, but not limited to, external pacemakers, cardioverter/defibrillators, pacer/defibrillators, biventricular or other multi-site coordination devices, monitors, programmers, and recorders.

Figure 1:
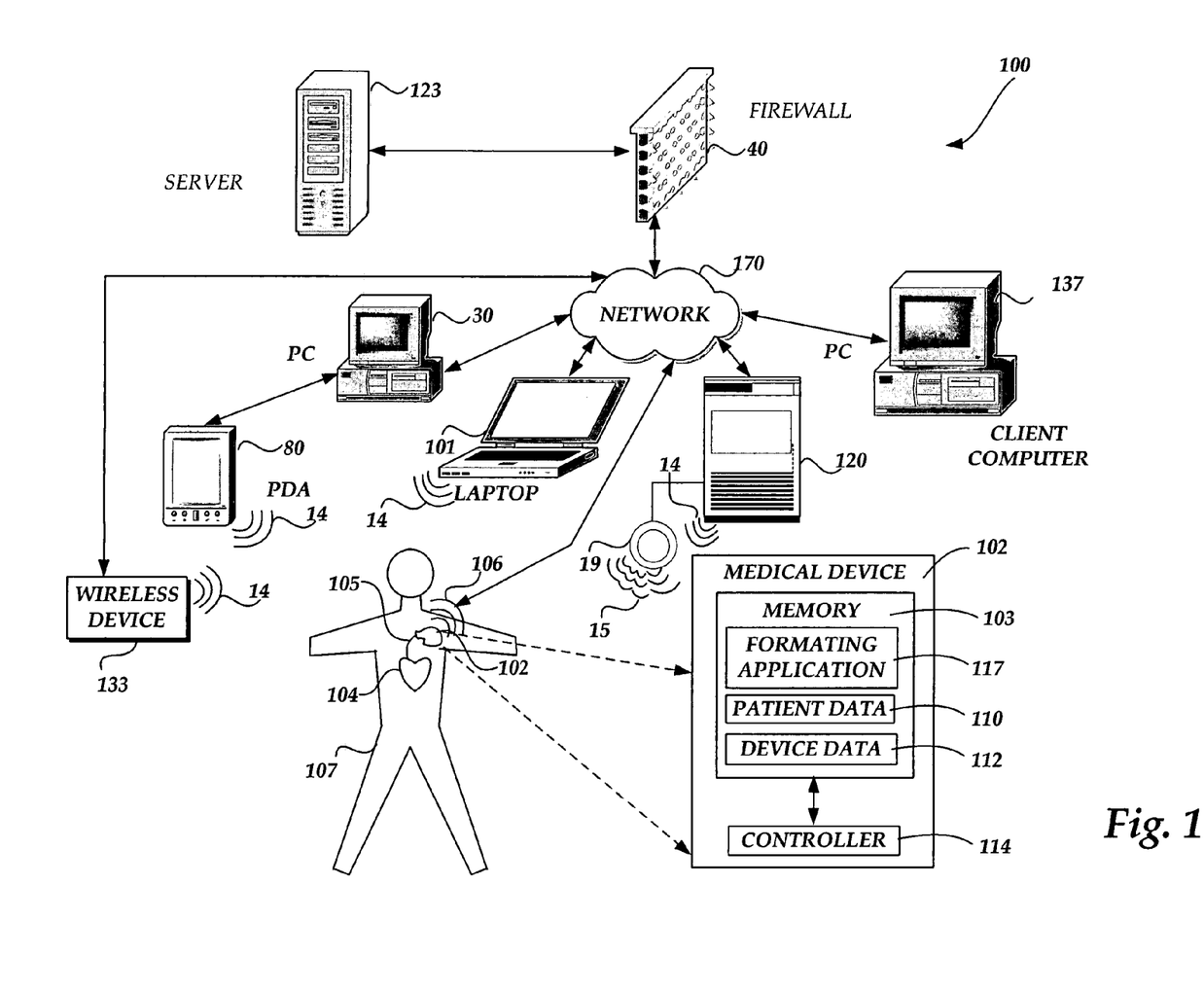
FIG. 1 is a schematic drawing illustrating components of an embodiment of the present invention and an operating environment in which the embodiment may be utilized.

Referring now to FIG. 1, a networked and/or wireless operating environment 100 utilized in embodiments of the present invention that allow an implantable medical device 102 to generate web content and communicate the web content to one or more external computing devices will be described. As shown in FIG. 1, the operating environment includes the medical device 102, such as an implantable pulse generator. The medical device 102 is implanted in a patient 107 and coupled to the heart 104 of the patient 107 by one or more leads 105. The medical device 102 includes a memory 103 and a controller 114. Stored on the memory 103 is a formatting application 117 for generating web content, patient data 110, and device data 112. The patient data 110 may include all patient diagnostic information. The device data 112 may include device information as well as information from other medical devices in communication with the implantable pulse generator, such as another implantable sensor. Additional details regarding the architecture of the implantable medical device 102 will be described below with respect to FIGS. 2-3.

The operating environment also includes portable computing devices or systems, such as a personal digital assistant (PDA) 80, an external programmer 120, a wireless device 133, such as a transceiver, and/or a laptop computer 101. Each portable device may serve as a patient, clinician, or physician terminal and are adapted to be communicatively coupled to the medical device 102. Each portable device radiates a wireless signal 14 and may receive wireless signal 106 from the implantable medical device 102. The external programmer 120 may also radiate a telephony signal 15 from an antenna 19. Any wireless protocol, such as microwave, cellular telephony, 802.11, may be used to transmit the web content from the IMD 102 to a portable device. Each portable device may also transmit data to a secure server computer 123 via the network 170. For instance, the PDA 8 may display web content received and/or dock with a personal computer (PC) 30 connected to the network 170, such as the Internet or Intranet. The PC 30 may upload the web content received from the implantable medical device 102 by the PDA 8 to the secure server 123 secured by a firewall 40 and/or display the web content received.

Alternatively, the laptop computer 101 or external programmer 120 may be communicatively coupled to the implantable medical device 102 via the wireless signals 14 and connected to the network 170. The laptop computer 101 or external programmer may receive web content via the wireless signal 106 and display the web content or upload the web content to the secure server 123. Also alternatively, the wireless device 133, such as a transceiver, may receive web content transmitted from the implantable medical device 102, whenever the IMD 102 is within a range of the wireless device 133. The wireless device may then upload the web content to the server computer 123 via the network 170.

Still alternatively, the IMD 102 may transmit the web content directly over the network to the server computer 123 or a client computer 137. For instance, a client computer 137 may initiate a request for information from the IMD 102 over the network 170. In response, either the server computer 123 or the IMD 102 may directly respond to the request by retrieving the requested information and communicating the information back to the client computer 137 via the network 170. Additional details regarding the generation and communication of web content will be described below in FIG. 7.

Figure 2:
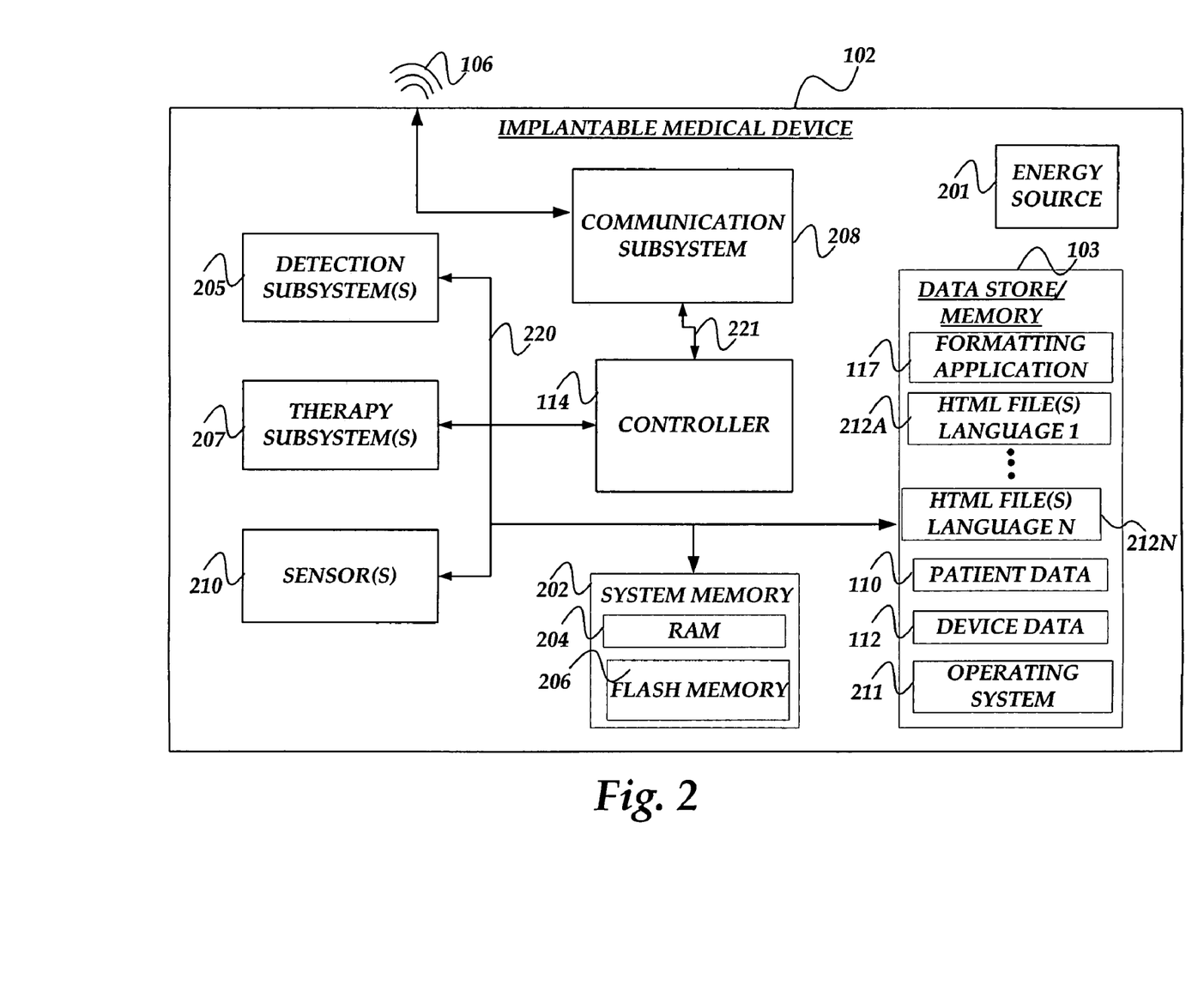
FIG. 2 illustrates a computing system architecture for an implantable medical device utilized in an embodiment of the present invention.

FIG. 2 shows a block diagram illustrating computing system architecture for the IMD 102 utilized in an embodiment of the present invention. The IMD 102 includes a communications subsystem 208, for example a telemetry module, a controller 114, an energy source 201, a system memory 202, and a system bus 220 that couples the system memory 202 to the controller 114. The system memory 202 includes flash memory 206 and random access memory (RAM) 204. The IMD 102 may also include a detection subsystem 205, a therapy subsystem 207, and sensor(s) 210. The IMD 102 further includes a data store/memory (DSM) 103 for storing an operating system 211, the formatting application 117, HTML output files 212A-212N generated by the formatting application 117, patient data 110, and device data 112. The HTML output files 212A-212N may or may not include template structures. It should also be appreciated that the operating system 211 may be a proprietary kernel/executive or a traditional operating system such as WINDOWS from Microsoft Corporation. The formatting application 117 in cooperation with the controller 114 is operative to generate and communicate web content from within the IMD 102. The formatting application 117 may also be stored in the flash memory 206 or RAM 204. The formatting application 117 converts patient data and/or device data collected in an unreadable format to the human eye into a human readable format in a structured output file, such as an HTML output file.

The DSM 103 is connected to the controller 114 through a mass storage controller (not shown) connected to the system bus 220. The DSM 103 and its associated computer-readable media, provide non-volatile storage for the IMD 102. Although the description of computer-readable media contained herein refers to a data storage device, such as a hard disk or CD-ROM drive, it should be appreciated by those skilled in the art that computer-readable media can be any available media that can be accessed by the controller 114.

The communications subsystem 208 receives signals from and sends signals to the controller 114 through the signal bus 220. The communications subsystem 208 may or may not use circuitry such as that known in the art for implantable device communications. The medical device 102 radiates a signal 106 that also has encoded information, such as web content being communicated from the IMD 102 to a portable device or over the network 170 to the server 123 and/or the client computer 137. The web content may be generated and communicated in the form of the HTML files 212A-212N. It should be appreciated that the web content may be generated and communicated in a variety of languages 1-N depending on the request for information and/or IMD 102 settings. The web content may then be consumed, transferred, and/or rendered by a standard web browser, such as NETSCAPE NAVIGATOR or INTERNET EXPLORER from MICROSOFT CORPORATION of Redmond, Wash.

The controller 114 may employ various operations, discussed in more detail below with reference to FIG. 8 to provide and utilize the signals propagated between the controller 114 and the communications subsystem 208. The controller 114 may store data to and access data from DSM 103, such as electronic memory or magnetic storage. Data may be collected via the detection subsystem 205, the therapy subsystem 207, and one or more sensors 210 which monitor the patient and the device and facilitate calculations and graphs illustrating the status of the patient and the device. Data is transferred to and received from the DSM 103 through the system bus 220. The controller 114 may be a general-purpose computer controller or processor typically used for an IMD. Furthermore, the controller 114 may be firmware, hard-wired logic, analog circuitry, other special purpose circuitry, or any combination thereof.

According to various embodiments of the invention, the IMD 102 operates in a networked and/or wireless environment, as shown in FIG. 1, using a wireless signal 106 to make logical connections with portable devices and remote computers through the network 170, such as the Internet, an Intranet, or a local area network (LAN). The IMD 102 may connect to the network 170 via the communications subsystem 208 connected to the signal bus 221. It should be appreciated that the communications subsystem 208 may also be utilized to connect to other types of networks and remote computer systems. The communications subsystem 208 may also serve as the interface for receiving and responding to information requests over the network 170.

A computing device, such as the IMD 102, typically includes at least some form of computer-readable media. Computer readable media can be any available media that can be accessed by the controller 114. By way of example, and not limitation, computer-readable media might comprise computer storage media and communication media.

Computer storage media includes volatile and nonvolatile, removable and non-removable media implemented in any method or technology for storage of information such as computer readable instructions, data structures, program modules or other data. Computer storage media includes, but is not limited to, RAM, ROM, EPROM, flash memory or other memory technology, CD-ROM, digital versatile disks (DVD) or other optical storage, magnetic cassettes, magnetic tape, magnetic disk storage or other magnetic storage devices, or any other medium that can be used to store the desired information and that can be accessed by the controller 114.

Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared, and other wireless media. Combinations of any of the above should also be included within the scope of computer-readable media. Computer-readable media may also be referred to as computer program product.

Figure 3:
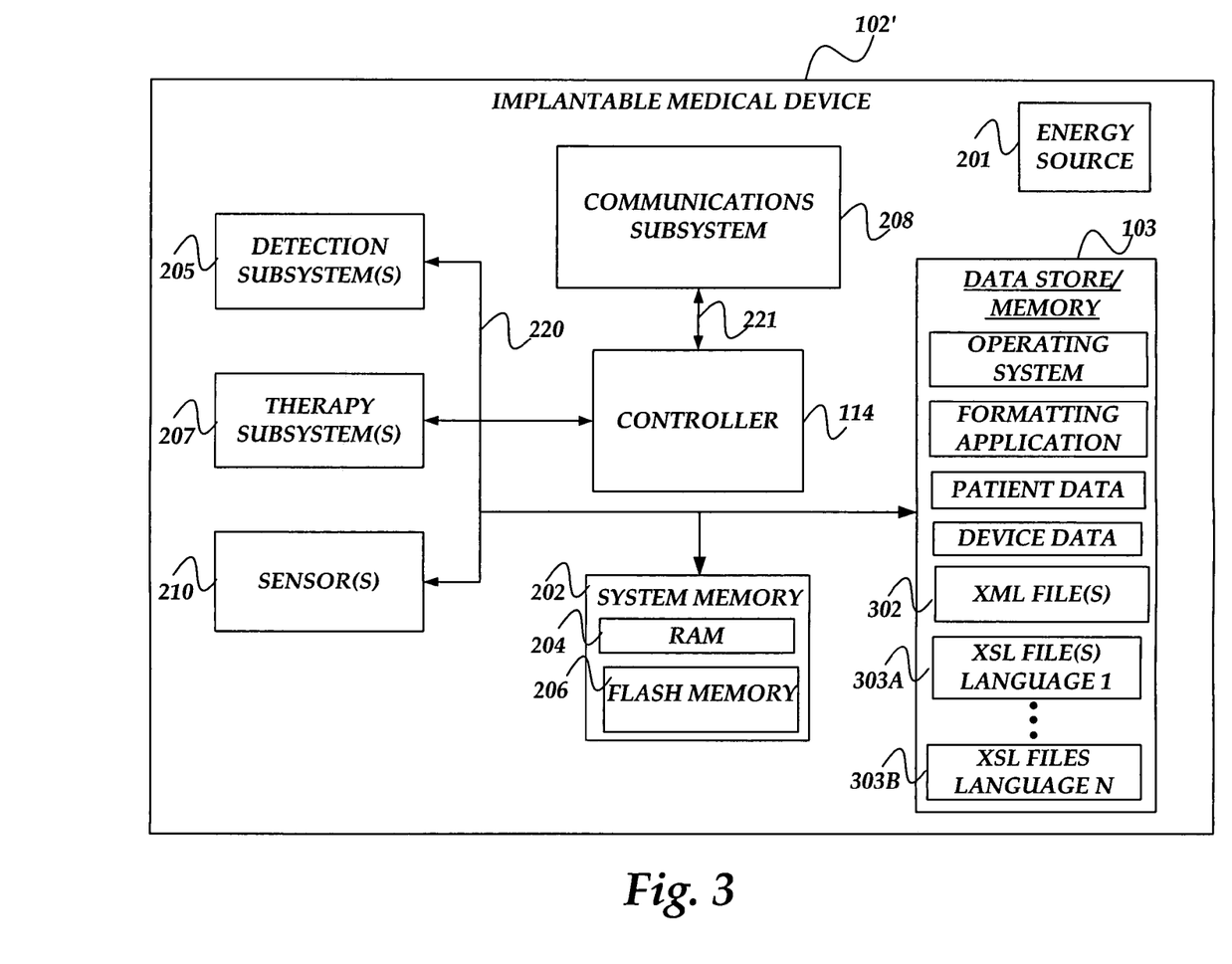
FIG. 3 illustrates a computing system architecture for an implantable medical device utilized in another embodiment of the present invention.

Turning now to FIG. 3, a block diagram illustrating a computing system architecture for an IMD 102' utilized in another embodiment of the present invention will be described. Here, the IMD 102' is similar to the IMD 102 with the exception of the type of human readable web content generated by the formatting application 117. The formatting application 117 converts the collected patient and device data to an XML format in the structure of the XML file(s) 302. Instructions for how to interpret XML files are provided in the form of XSL files 303A-N. XSL files are a specification for separating style from content when creating XML pages. Instructions may also include technologies such as JAVA and JAVASCRIPT from Sun Microsystems, PERL developed by Larry Wall and other similar scripting languages for interpreting information. It should be appreciated that the XML files 302 may be generated in a variety of languages 1-N depending on the request for information and/or the settings of the IMD 102' which determines the XSL file 303A-303N that will be transmitted with the XML file 302. In the alternative, the XSL files may be located on the portable devices, the client computer 137, and/or the server computer 123.

Figure 4:
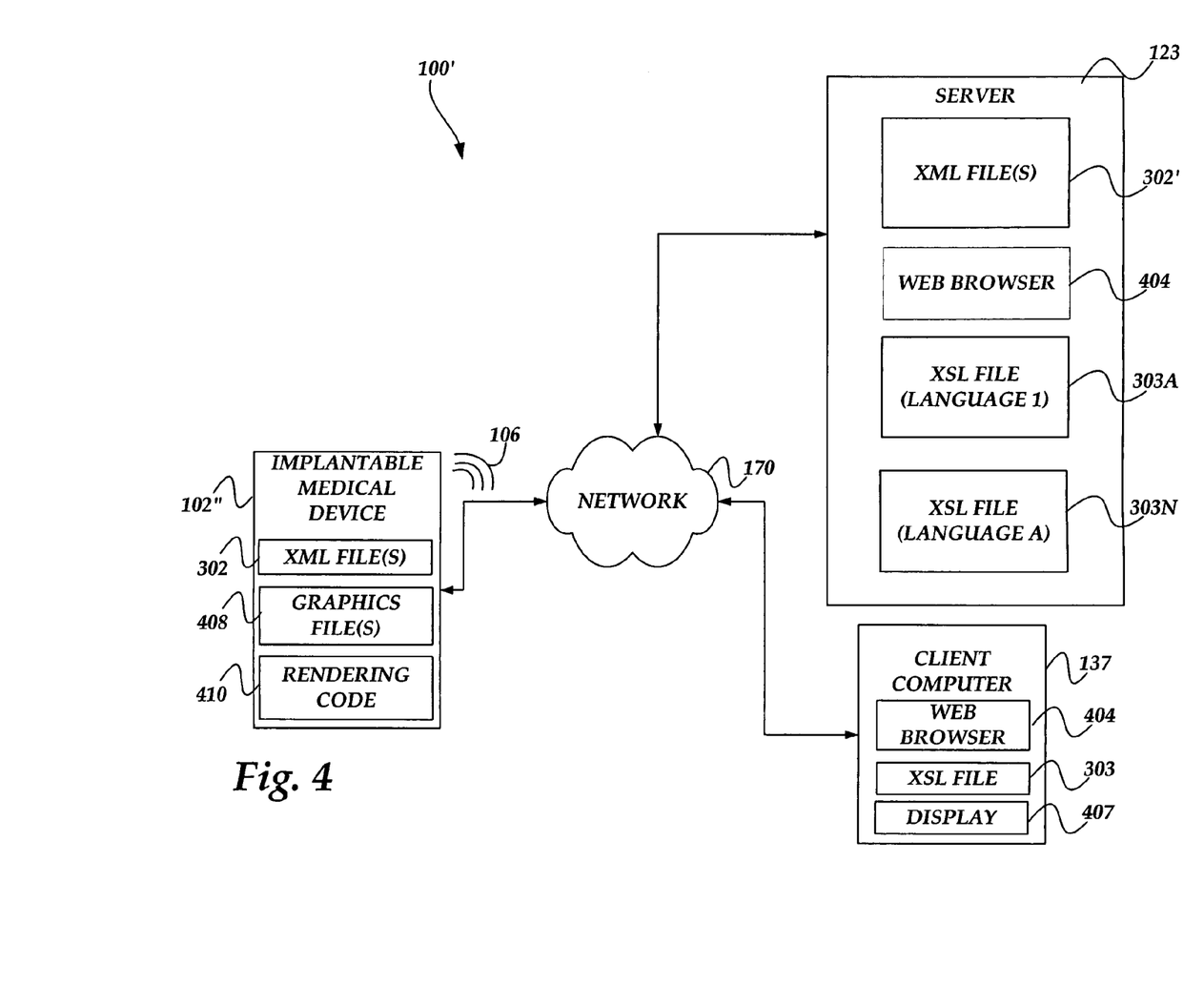
FIG. 4 illustrates an operating environment and computing system architecture for a client computer and server computer utilized in an embodiment of the present invention.

Referring to FIG. 4, a block diagram illustrating the operating environment 100' and a computing system architecture for the client computer 137 and server computer 123 utilized in an embodiment of the present invention will be described. In FIG. 4 the IMD 102" interfaces directly with the server computer 123 and/or the client computer 137 over the network 170. The client computer 137 may be a standard personal computer that includes a standard web browser 404, such as NETSCAPE NAVIGATOR. The client computer 137 may initiate a request for information from the IMD 102", by receiving a selection of a web page link via an interface of the client computer 137. The IMD 102" will receive the request for web content over the network 170, collect the requested data, convert the data to a human readable format, such as XML, populate a structure of the XML file 302, and transmit the XML file 302 to the client computer 137. In should be appreciated that the XSL file 303 may also reside on the client computer 137 and provide instructions for interpreting the XML file 302 upon arrival of the XML file at the client computer 137.

Alternatively, the client computer 137 may request the information from the server computer 123 which may store information from around the world concerning IMDs. Here the client computer 137 may retrieve the XML file 302' from the server 123 using the web browser 404 and interpret and render the XML file 302' using the web browser 404, the XSL file 303 or the XSL file 303A-303N from the server 123 depending on the language desired. The XML page may be rendered and displayed via the display device 407 of the client computer 137. It should be further appreciated that when the web content includes graphics, such as a graphics file 408, helper or rendering code 410 should be read from the IMD 102" and executed by the client computer 137 in order to render the graphics file 408. The rendering code 410 may also include interactive components. It should be appreciated that the graphic file 408 may be generated within the IMD 102.

Figure 5:
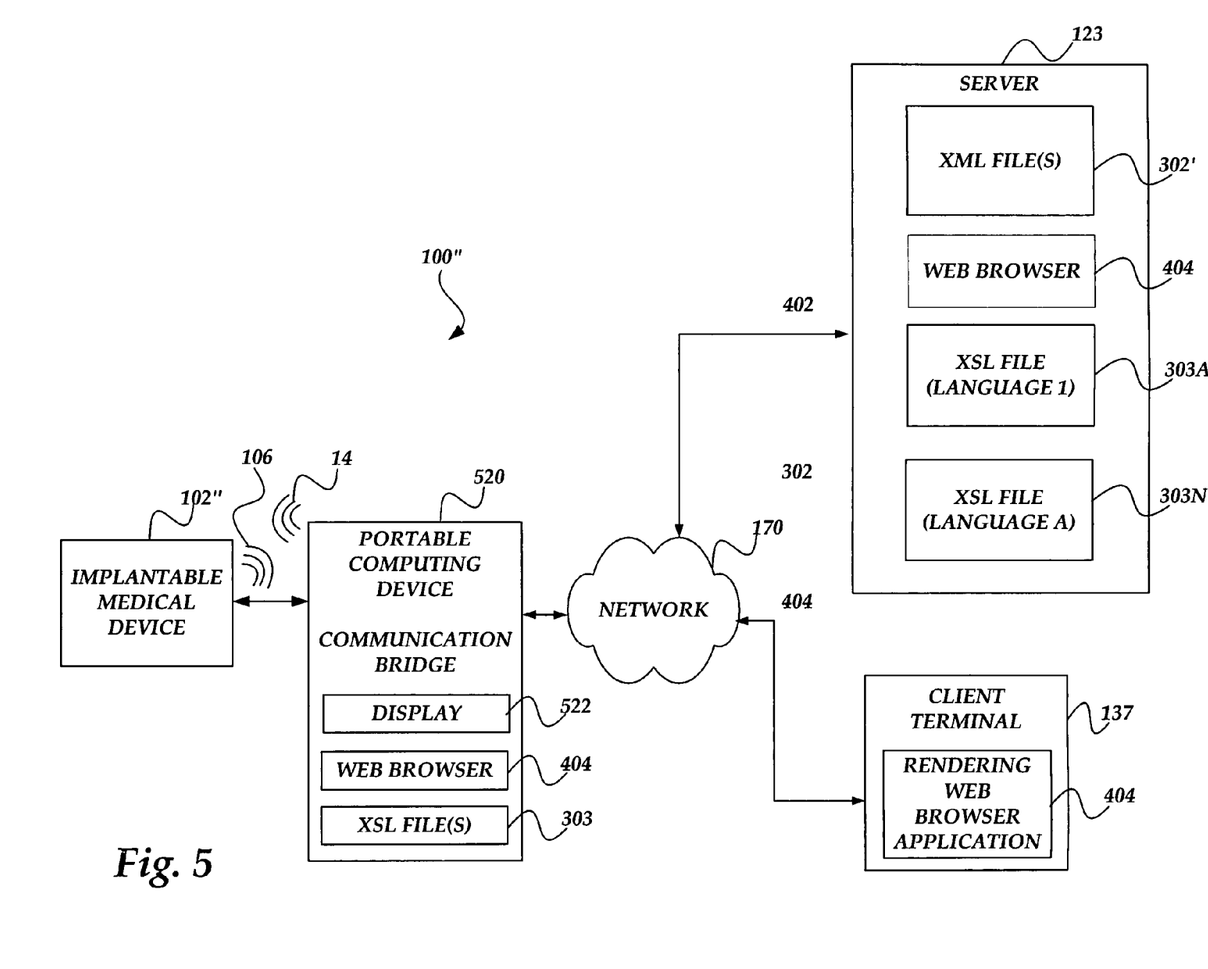
FIG. 5 illustrates an operating environment and computing system architecture for a client computer and server computer utilized in another embodiment of the present invention.

FIG. 5 shows a block diagram illustrating the operating environment 100" and a computing system architecture for the client computer 137 and server computer 123 of FIG. 4 utilized in another embodiment of the present invention. Here the operating environment 100" further includes a portable computing device 520 serving as a communication bridge to the network 170. The portable computing device 520 may embody any of the portable computing devices described in FIG. 1. In the present embodiment, the portable computing device 520 may submit a request to the IMD 102" utilizing the web browser 404 via the radiated signal 14. In response, the IMD 102" collects, converts and communicates the requested information in human readable format to the portable device 520 via the radiated signal 106. The portable device may display the web content via the display 522 using the XSL file 303 store on the portable device 520 and/or forward the web content to the server 123 for storage as the XML file(s) 302'. The portable device 520 may also forward the web content to the client computer 137 for rendering via the display 407. Additional details regarding the portable computing device 520 will be described below with respect to FIG. 6.

Figure 6:
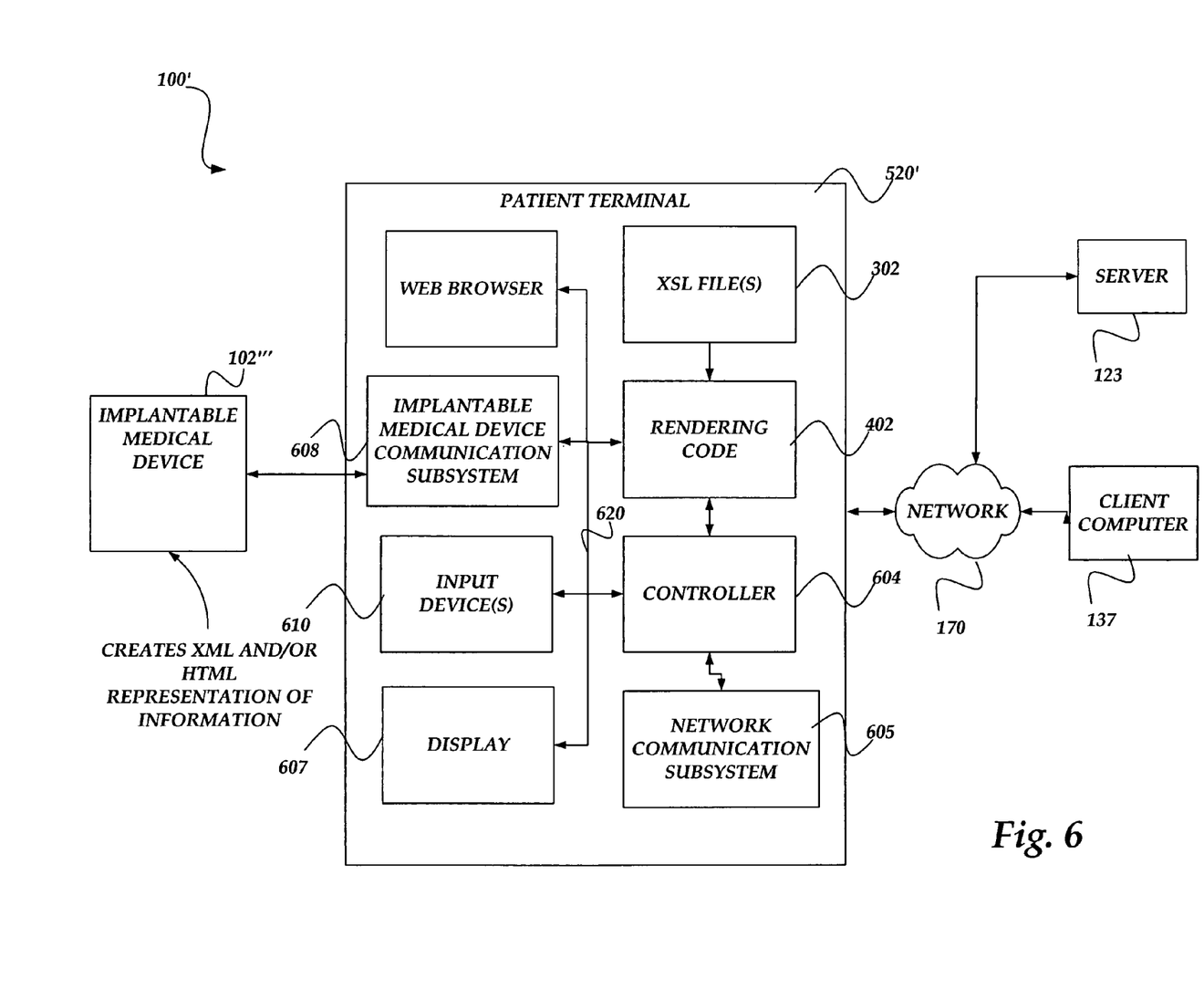
FIG. 6 illustrates an operating environment and a computing system architecture for a patient/clinician terminal utilized in an embodiment of the present invention.

Referring now to FIG. 6, a block diagram illustrating the operating environment 100" and a computing system architecture for a patient/clinician terminal 520' utilized in an embodiment of the present invention will be described. The radiated signal 106 propagated from the IMD 102''' is received by the terminal 520' and is converted to an electrical signal that is transferred to the IMD communications subsystem 608. The IMD communications subsystem 608 may then employ an analog-to-digital conversion to convert the received signal 106 to a data signal that is then passed to the controller 604. It should be appreciated that the IMD 102''' may generate web content in HTML and/or XML format.

Alternatively, or in addition to feeding received signals to the controller 604, the IMD communications subsystem 608 may feed signals directly to the display device 607 for real-time display of the information encoded on the signal 106 such as the web content in HTML or XML. The controller 604 may also transfer a display signal to the display device 607 through the system bus 620. The display signal may include an information signal produced by the IMD communications subsystem 608. The input controller 610 may also be included with the terminal 520' for receiving and processing input from a number of input devices, including a keyboard, audio and/or voice input, a stylus and/or mouse (not shown).

It should be appreciated that in this embodiment that the XSL file(s) 303 and the rendering code 410, described above with respect to FIGS. 3 and 4 respectively, are stored on the terminal 520'. Thus, instructions on interpreting the XML files 302 and rendering code for displaying graphics files 408 originate with the terminal 520'. The web content may subsequently be transmitted to the server 123 and/or the client computer 137 via the network communications subsystem 605 over the network 170.

Figure 7:
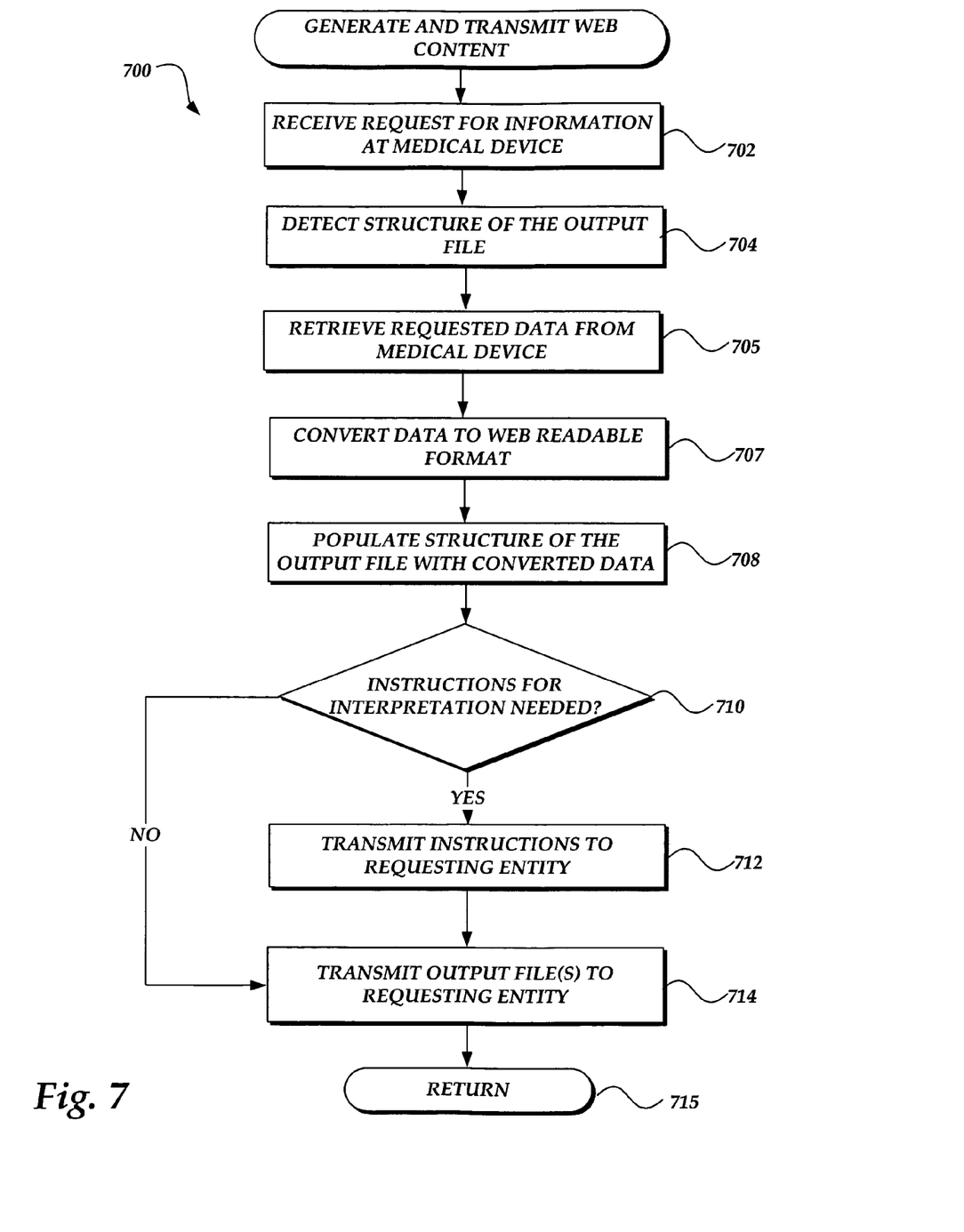
FIG. 7 illustrates an operational flow performed in generating and communicating web content from within an implantable medical device in an embodiment of the present invention.

Turning now to FIG. 7, an operational flow performed in generating and communicating web content from within an implantable medical device in an embodiment of the present invention will be described. The operational flow 700 begins at receive operation 702 where a request for information is received at the IMD 102. This request may be in the form of a hyperlink being selected on a portable device or client computer communicatively coupled to the IMD 102 via a wireless signal.

The operational flow 700 then continues to detect operation 704 where the IMD 102 detects the structure of the web content output file. The structure is detected in order to identify how to populate the structure, for example XML schema of the XML file.

The operational flow 700 then continues to retrieve operation 705 where data is collected from the memory and or subsystems of the IMD 102. The collected data may include information on patient status, medical device status, and medical device settings. This data may be collected while the IMD 102 is operating within a patient and/or in storage away from the patient. Next, the operational flow 700 continues to convert operation 707 where the collected data is converted to a web readable or human readable format. Here, the unrecognizable form in which the data is collected is converted to a web readable format, such as HTML, XML, JPEG, and/or SGML. (Other graphics file formats are equally applicable, such as GIF, TIFF, etc.)

The operational flow 700 then continues to populate operation 708 where the structure detected is populated with the converted data. An output file structured for web interface presentation is produced from the operation 708. The operational flow then proceeds to detect operation 710 where a determination is made as to whether instructions for how to interpret the output file are needed. For instance, when the output file is made up of XML schema, an XSL file is needed to provide instructions to the web browser on how to interpret the XML file. However, when the output file is an HTML file instructions for how to interpret the converted data, for example XSL files, are not needed. When it is determined that instructions form interpretation are not needed, the operational flow 700 continues to transmit operation 174 described below. When it is determined that instructions for interpretation are needed, the operational flow 700 continues to transmit operation 712.

At transmit operation 712 the instructions for interpretation stored on the IMD 102 are transmitted to the requesting entity to inform the web browser how to interpret the XML or output file. Next, the operational flow 700 continues to transmit operation 714 where the output file is transmitted to the requesting entity for interpretation, storage, and/or display. It should be appreciated that in the alternative the web content may be automatically reported to a server, where it is buffered for a later request. The operational flow 700 then continues to return operation 715 where control is returned to other routines.

Thus, the present invention is presently embodied as methods, systems, computer program products or computer readable mediums encoding computer programs for generating and communicating web content from within an implantable medical device.

As various changes may be made in the above system elements, software modules and methods without departing from the scope of the invention, it is intended that all matter contained in the above description as shown in the accompanying drawings shall be interpreted as illustrative and not in a limiting sense. Since many embodiments of the invention can be made without departing from the spirit and scope of the invention, the invention resides in the claims hereinafter appended.

I claim:

1. A method for generating and communicating web content from within an implantable medical device, the method comprising:
    collecting data from at least one of a memory and a subsystem of an implantable medical device; and
    converting the data into web content having a web readable format selectable from a plurality of web readable format types that is readily consumable for display via a web interface thereby providing a web server from within the implantable medical device;
    determining, according to the web readable format type, whether instructions are required for interpreting the converted data; and requesting instructions for the interpretation of the converted data from the implantable medical device
    transmitting instructions from the implantable medical device to a computing apparatus requested.

2. The method of claim 1, further comprising at least one of the following:
    reporting the web content to a computing apparatus for later retrieval; and
    receiving a request for the data at the implantable medical device, wherein the data is collected in response to receiving the request.

3. The method of claim 1, further comprising detecting a structure of an output file wherein converting the data into web content includes populating the structure of the output file with the data converted into the web content.

4. The method of claim 3, wherein the output file is stored in the memory of the implantable medical device, the method further comprising transmitting the output file to the computing apparatus.

5. The method of claim 4, further comprising transmitting instructions for interpreting the output file to the computing apparatus.

6. The method of claim 4, wherein the web readable format comprises a markup language.

7. The method of claim 4, wherein the web readable format comprises at least one of the following:
    HTML (Hyper Text Markup Language);
    JPEG (Joint Photographic Experts);
    GIF (Graphic Interchange Format);
    TIFF (Tagged Image File Format);
    XML™ (eXtensible Markup Language); and
    SGML™ (Standard Generalized Markup Language).

8. The method of claim 6, wherein the web readable format comprises at least one of HTML and XML and wherein instructions for interpreting the output file are stored on one of the computing apparatus and the implantable medical device, the method further comprising transmitting the instructions to the computing apparatus when the instructions are stored on the implantable medical device.

9. The method of claim 8, wherein the web readable format comprises XML and wherein the instructions comprise at least one XSL file.

10. The method of claim 4, wherein the web readable format includes graphics data and wherein rendering code, executed in order to at least one of render the graphics data and provide interactive components via the web interface, is stored on one of the computing apparatus and the implantable medical device.

11. The method of claim 10, wherein the rendering code is stored on the implantable medical device further comprising transmitting the rendering code to the computing apparatus.

12. The method of claim 11, wherein the rendering code includes directions to publish the web content in a specified language wherein the specified language is at least one of:
    selected from a variety of languages,
    determined based on a location of the web interface displaying the web content;
    determined upon installation of the implantable medical device; and
    specified in a request.

13. The method of claim 8, wherein the instructions include directions to publish the web content in a specified language, wherein the specified language is at least one of:
    selected from a variety of languages,
    determined based on a location of the web interface;
    determined upon installation of the implantable medical device; and
    specified in a request.

14. The method of claim 9, wherein a memory of one of the computing apparatus and the implantable medical device stores an XSL file for each language available designating a specified language associated with the XSL file.

15. The method of claim 1, wherein collecting the data comprises collecting at least one of the following:
- patient status data;
- medical device status data; and
- medical device settings data wherein the data is collected while the implantable medical device is one of operating and in storage.

16. A computer program product comprising a computer usable medium having control logic stored therein for causing a pulse generator to generate and communicate web content, the control logic comprising computer readable program code for causing the pulse generator to:
- collect data from a memory of the pulse generator; and
- convert the data into web content having a web readable format selectable from a plurality of web readable format types that is readily consumable for display via a web interface;
- determine, according to the web readable format type, whether instructions are required for interpreting the converted data; and requesting instructions for the interpretation of the converted data from the implantable medical device
- transmit instructions from the implantable medical device to a computing apparatus when requested.

17. The computer program product of claim 16, further comprising computer program code for causing the pulse generator to receive a request for the data wherein the data is collected in response to receiving the request.

18. The computer program product of claim 16, further comprising computer program code for causing the pulse generator to detect a structure of an output file and populate the structure of the output file with the data converted into the web content.

19. The computer program product of claim 16, wherein the output file is stored in the memory of the pulse generator, further comprising computer program code for causing the pulse generator to transmit the output file to the computing apparatus.

20. The computer program product of claim 19, wherein the web readable format comprises a markup language.

21. The computer program product of claim 16, wherein the instructions comprise at least one XSL file.

22. The computer program product of claim 19, wherein the web readable format includes graphics data further comprising computer program code for causing the pulse generator to transmit rendering code to the computing apparatus in order to at least one of help render the graphics data and provide interactive components via the web interface.

23. The computer program product of claim 22, wherein the rendering code includes directions to publish the web content in a specified language.

24. The computer program product of claim 16, wherein the instructions include directions to publish the web content in a specified language.

25. The computer program product of claim 16, wherein the data collected comprises at least one of the following:
- patient status data;
- medical device status data; and
- medical device settings data wherein the data is collected while the pulse generator is one of operating and in storage.

26. A system for generating and communicating web content from within an implantable medical device, the system comprising:
the implantable medical device having a memory, the implantable medical device operative to:
- collect data from the memory; and
- convert the data into web content having a web readable format selectable from a plurality of web readable format types that is readily consumable for display via a web interface;
- determine, according to the web readable format type, whether instructions are required for interpreting the converted data; and requesting instructions for the interpretation of the converted data from the implantable medical device
- transmit instructions from the implantable medical device to a computing apparatus requested.

27. The system of claim 26, wherein the implantable medical device is further operative to receive a request for the data, wherein the data is collected in response to receiving the request, the request initiated by one of selecting a link via a web interface and a scheduled triggering event.

28. The system of claim 26, wherein the implantable medical device is operative to detect a structure of an output file and populate the structure of the output file with the data converted into the web content.

29. The system of claim 26, further comprising the first computing apparatus wherein the implantable medical device is further operative to transmit the output file to the first computing apparatus.

30. The method of claim 26, wherein the web readable format comprises a markup language and wherein at least one of one of the computing apparatus and the implantable medical device is further operative to store an XSL file for each language available to display the web content each XSL file designating a specified language associated with the XSL file.

31. The system of claim 29, further comprising a second computing apparatus wherein the first computing apparatus is operative to at least one of:
- receive and forward the output file to a second computing apparatus for at least one of storage, retrieval, and display via a web interface of the second computing apparatus; and
- interpret and display the web content from the output file via a display device of the first computing apparatus.

32. The system of claim 31, wherein the first computing apparatus comprises a wireless device operatively in communication with at least one of a network and the second computing apparatus.

33. The system of claim 31, wherein the first computing apparatus comprises at least one of the following:
- a personal digital assistant;
- a laptop computer; and
- an external programmer.

34. The system of claim 33, wherein the second computing apparatus comprises at least one of a personal computer and a server computer.

* * * * *

UNITED STATES PATENT AND TRADEMARK OFFICE
CERTIFICATE OF CORRECTION

PATENT NO. : 7,353,063 B2 Page 1 of 1
APPLICATION NO. : 11/020937
DATED : April 1, 2008
INVENTOR(S) : Simms It is certified that error appears in the above-identified patent and that said Letters Patent is hereby corrected as shown below:

In column 9, line 65, in Claim 1, after "apparatus" insert -- when instructions are --.

In column 10, line 22, in Claim 7, delete "(Joint Photographic Experts);" and insert -- (Joint Photographic Experts Group); --, therefor.

In column 11, line 24, in Claim 16, after "when" insert -- instructions are --.

In column 12, line 18, in Claim 26, after "apparatus" insert -- when instructions are --.

In column 12, line 34, in Claim 30, before "the computing" delete "one of".

Signed and Sealed this

Fifteenth Day of July, 2008

JON W. DUDAS
*Director of the United States Patent and Trademark Office*